(12) United States Patent
Nakada et al.

(10) Patent No.: US 10,371,677 B2
(45) Date of Patent: Aug. 6, 2019

(54) ODOR ADSORBENT MATERIAL, ODOR DETECTION KIT, AND METHOD FOR USING SAME

(71) Applicants: SUNTORY HOLDINGS LIMITED, Osaka (JP); TOPPAN PRINTING CO., LTD., Tokyo (JP)

(72) Inventors: Takiko Nakada, Osaka (JP); Ryoichi Tajima, Osaka (JP); Masanobu Yoshinaga, Tokyo (JP)

(73) Assignees: SUNTORY HOLDINGS LIMITED, Osaka (JP); TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 14/379,412

(22) PCT Filed: Mar. 26, 2013

(86) PCT No.: PCT/JP2013/002038
§ 371 (c)(1),
(2) Date: Aug. 18, 2014

(87) PCT Pub. No.: WO2014/045478
PCT Pub. Date: Mar. 27, 2014

(65) Prior Publication Data
US 2015/0037906 A1 Feb. 5, 2015

(30) Foreign Application Priority Data
Sep. 18, 2012 (JP) .................. 2012-204369

(51) Int. Cl.
*G01N 1/22* (2006.01)
*G01N 33/00* (2006.01)
(Continued)

(52) U.S. Cl.
CPC ..... *G01N 33/0001* (2013.01); *B01D 53/0407* (2013.01); *B01J 20/18* (2013.01);
(Continued)

(58) Field of Classification Search
CPC ............ A61B 10/0038; A61B 10/0045; A61B 10/0051; C12M 1/26; C12M 1/28;
(Continued)

(56) References Cited

U.S. PATENT DOCUMENTS 5,186,831 A * 2/1993 DePetris .................... 210/242.4
5,186,900 A * 2/1993 Jensen et al. ................ 422/550
(Continued)

FOREIGN PATENT DOCUMENTS

CA 2243801 5/1999
CN 101672837 A 3/2010
(Continued)

OTHER PUBLICATIONS

English Translation of a Korean Office Action dated Oct. 2, 2014 in corresponding Korean Patent Application No. 2014-7023434.
(Continued)

*Primary Examiner* — Jill A Warden
*Assistant Examiner* — Dwayne K Handy (57) ABSTRACT

An odor adsorbent material, an odor detection kit, and a method for using the same for rapidly identifying a facility where binding of an odor component had occurred among facilities used in a distribution route of a commodity. The odor detection kit includes at least two pieces of an odor adsorbent material, a package section that includes at least two storage sections and is configured to store the odor adsorbent material, and a sheet section. The odor detection kit is installed in a facility. At least one of the pieces of the odor adsorbent material is exposed to open space in the facility, recovered therefrom, and sealed and stored. At the
(Continued)

time of testing, occurrence of odor emission in the facility is determined by comparing odor components adsorbed by each of the pieces of the odor adsorbent material.

15 Claims, 5 Drawing Sheets

(51) Int. Cl.
| | |
|---|---|
| *B01D 53/04* | (2006.01) |
| *B01J 20/18* | (2006.01) |
| *B01J 20/20* | (2006.01) |
| *B01J 20/26* | (2006.01) |
| *B01J 20/28* | (2006.01) |
| *G01N 33/02* | (2006.01) |
| *B32B 25/08* | (2006.01) |
| *B32B 27/32* | (2006.01) |

(52) U.S. Cl.
CPC .............. *B01J 20/20* (2013.01); *B01J 20/261* (2013.01); *B01J 20/262* (2013.01); *B01J 20/28035* (2013.01); *B32B 25/08* (2013.01); *B32B 27/32* (2013.01); *G01N 33/02* (2013.01); *B01D 2253/102* (2013.01); *B01D 2253/108* (2013.01); *B01D 2253/20* (2013.01); *B01D 2253/202* (2013.01); *B01D 2257/90* (2013.01); *B01J 2220/46* (2013.01); *G01N 1/2214* (2013.01); *Y10T 29/49815* (2015.01); *Y10T 29/49826* (2015.01)

(58) Field of Classification Search
CPC ......... C12M 1/30; G01N 1/22; G01N 1/2214; G01N 2001/2276; G01N 2001/2285; G01N 2001/2876; B01D 53/0407; B01D 2253/00; B01D 2253/20; B01D 2253/202
USPC ................................ 422/406, 408, 409, 411
See application file for complete search history.

(56) References Cited

U.S. PATENT DOCUMENTS

| | | | | |
|---|---|---|---|---|
| 5,517,866 | A * | 5/1996 | Manning | G01N 1/2273 73/863.21 |
| 5,698,774 | A * | 12/1997 | Osmanski | 73/61.43 |
| 5,922,974 | A * | 7/1999 | Davison et al. | 73/864.74 |
| 6,019,823 | A * | 2/2000 | Tischler et al. | 96/108 |
| 6,565,808 | B2 * | 5/2003 | Hudak et al. | 422/411 |
| 6,706,531 | B1 * | 3/2004 | Haeseler et al. | 436/139 |
| 7,264,776 | B2 * | 9/2007 | Guo et al. | 422/411 |
| 8,852,531 | B2 * | 10/2014 | Gerritse et al. | 422/534 |

FOREIGN PATENT DOCUMENTS

| | | |
|---|---|---|
| CN | 101852692 A | 10/2010 |
| CN | 201654013 | 11/2010 |
| CN | 102288455 A | 12/2011 |
| DE | 197 51 363 A1 | 6/1999 |
| JP | 2001-121195 | 5/2001 |
| JP | 2006-288982 | 10/2006 |
| JP | 2011-169787 | 9/2011 |
| JP | 2012-102258 | 5/2012 |

OTHER PUBLICATIONS

Taiwanese Office Action dated Sep. 16, 2014 in corresponding Taiwanese Patent Application No. 102133758 (4 pages) (2 pages English Translation).
"*Influence of the polyethylene packaging on the adsorption of odour-active compounds from UHT-milk*"; Michael Czerny, Peter Schieberle; European Food Research Technology, vol. 225, pp. 215-223, Jun. 2007 (8 pages).
Chinese Office Action dated Jun. 1, 2015 in corresponding Chinese Patent Application No. 201380010908.4.
Extended European Search Report dated Feb. 19, 2015 in corresponding European Patent Application No. 13840030.4.
Taiwanese Office Action dated Feb. 11, 2015 in corresponding Taiwanese Patent Application No. 102133758.
U.S. Office Action dated Jul. 5, 2017 in related U.S. Appl. No. 15/250,401.
Non-Final Office Action dated Jan. 11, 2019 in U.S. Appl. No. 15/250,401 (13 pages).
Ryoichi Tajima et al., "Investigation of Off-flavor Sorption to External Can Wall", *The Society of Packaging Science and Technology*, Jul. 2000, pp. 74-75.
International Search Report dated Jun. 11, 2013, in corresponding International Patent Application No. PCT/JP2013/002038.

* cited by examiner

ODOR ADSORBENT MATERIAL, ODOR DETECTION KIT, AND METHOD FOR USING SAME

CROSS-REFERENCE TO RELATED APPLICATIONS

This application is a U.S. National Stage Application under 35 U.S.C. 371 of International Patent Application No. PCT/JP2013/002038, filed Mar. 26, 2013, which claims foreign priority to Japanese Patent Application No. 2012-204369, filed Sep. 18, 2012, all of which are incorporated herein by reference.

BACKGROUND

Field

The present invention relates to an odor adsorbent material for adsorbing offensive smell components, and further relates to an odor detection kit containing the odor adsorbent material and a method for using the odor detection kit.

Description of Related Art

Commodities such as food products have a risk of developing a quality problem caused when various odor components bind thereto in processes related to distribution such as production, transportation, and storage. For the purpose of removing this risk, packaging materials configured to reduce penetration of odor components and deodorization devices for containers have been proposed (cf. Patent Literature 1 and 2).

PATENT LITERATURE

Patent Document 1: Japanese Laid-Open Patent Publication No. 2012-102258
Patent Document 2: Japanese Laid-Open Patent Publication No. 2001-121195

SUMMARY

Even with improved packaging materials and odor adsorbent materials, it is difficult to completely prevent binding of odor components to commodities, and a small amount of an odor component may penetrate the packaging material and bind to some of the commodities. Thus, odor tests and commodity sampling tests etc., are performed in facilities used for production and distribution. Such facilities include warehouses, containers, and factories used in each of the processes involved in distribution such as production, transportation, and storage. Commodities that might have an odor component bound thereto are discovered and removed as much as possible, and if a quality problem has occurred by any chance, the process at which the binding of an odor component had occurred is identified to prevent recurrence. In order to take response measures rapidly, it is expected to immediately identify the facility where binding of an odor component had occurred.

Thus, an objective of the present invention is to enable rapid identification of a facility where binding of an odor component had occurred among facilities used in a distribution route of a commodity such as food products.

One aspect of the present invention is an odor detection kit including: at least two pieces of an odor adsorbent material; a package section that includes at least two storage sections and is configured to store the odor adsorbent material; and a sheet section.

Each of the pieces of the odor adsorbent material is sealed in one of the storage sections before being used, and at least one of the pieces of the odor adsorbent material is exposed to external open space when being used.

The odor adsorbent material preferably adsorbs substances having a bad odor or a sweet smell, including mold odor components including haloanisoles such as 2,4,6-trichloroanisole and 2,4,6-tribromoanisole, insect repellents such as naphthalene, agricultural chemicals or fragrances. Furthermore, the odor adsorbent material is formed from a sheet material containing a resin, and may be formed in particular by laminating polyethylene on both sides of an elastomer film.

At least one of the pieces of the odor adsorbent material is exposed for adsorbing an odor component, and is then sealed in one of the storage sections.

Another aspect of the present invention is a method for installing an odor detection kit. The method includes: attaching the odor detection kit in a facility for production or distribution of a commodity, and exposing at least one piece of the odor adsorbent material to open space in the facility; and entering, in the sheet section, information that specifies at least a time when the odor detection kit has been installed. Furthermore, this method may be conducted when transporting a commodity in the facility. Furthermore, the method may further include entering, in the sheet section, information that specifies the facility.

Another aspect of the present invention is a method for recovering an odor detection kit. The method includes: removing the odor detection kit installed in the facility for production or distribution of a commodity; storing and sealing, in one of the storage sections in which another piece of the odor adsorbent material is not sealed among the storage sections, one piece of the odor adsorbent material exposed to open space in the facility; entering, in the sheet section, information that specifies at least a time when the odor detection kit has been recovered; and, after the sealing and the entering, sealing the odor detection kit in a pouch material that has barrier property and odorless property. Furthermore, the method may be conducted when transporting a commodity out of the facility. Furthermore, the method may further include entering, in the sheet section, information that specifies the facility.

Another aspect of the present invention is a method for testing the odor detection kit. The method includes removing the pieces of the odor adsorbent material from the odor detection kit, and testing and comparing odor components adsorbed by each of the pieces of the odor adsorbent material. The method preferably further includes: specifying, based on an identification number given to a commodity, a facility used in production and distribution processes of the commodity and a time of usage; and selecting the odor detection kit that is to be a subject for testing, based on the specified facility and time of usage, and information that specifies a time of usage and a facility entered in the sheet section of the odor detection kit.

Another aspect of the present invention is an odor testing method. The method includes: preparing at least one piece of an odor adsorbent material packaged in a condition that prevents odor adsorption; installing, in a facility for production or distribution of a commodity, a piece of the odor adsorbent material in an exposed state; recovering the piece of the odor adsorbent material installed in the facility; and testing at least odor components adsorbed by the recovered piece of the odor adsorbent material.

With the present invention, it is possible to rapidly identify a facility where binding of an odor component had occurred among facilities used in a distribution route of a commodity such as food products.

DESCRIPTION OF EMBODIMENTS

In the following an embodiment of the present invention will be described.

1. Odor Adsorbent Material

As an odor adsorbent material, a resin, a paper, or the like may be used by itself, or a laminated body thereof may be used. Furthermore, a resin, a paper, or the like by itself, or a laminated body thereof may be used as a base material, and an odor adsorptive material such as activated carbon and zeolite may be kneaded therein. Examples of the resin that can be used include polyethylene, polypropylene, polymethylpentene, polyvinyl chloride, polystyrene, polyamide, polyacetal, acrylic resins, polycarbonate, polyethylene terephthalate, polybutylene terephthalate, styrene based elastomers, olefin based elastomers, vinyl chloride based elastomers, polyester based elastomers, polyurethane based elastomers, and nylon based elastomers.

Figure 1:
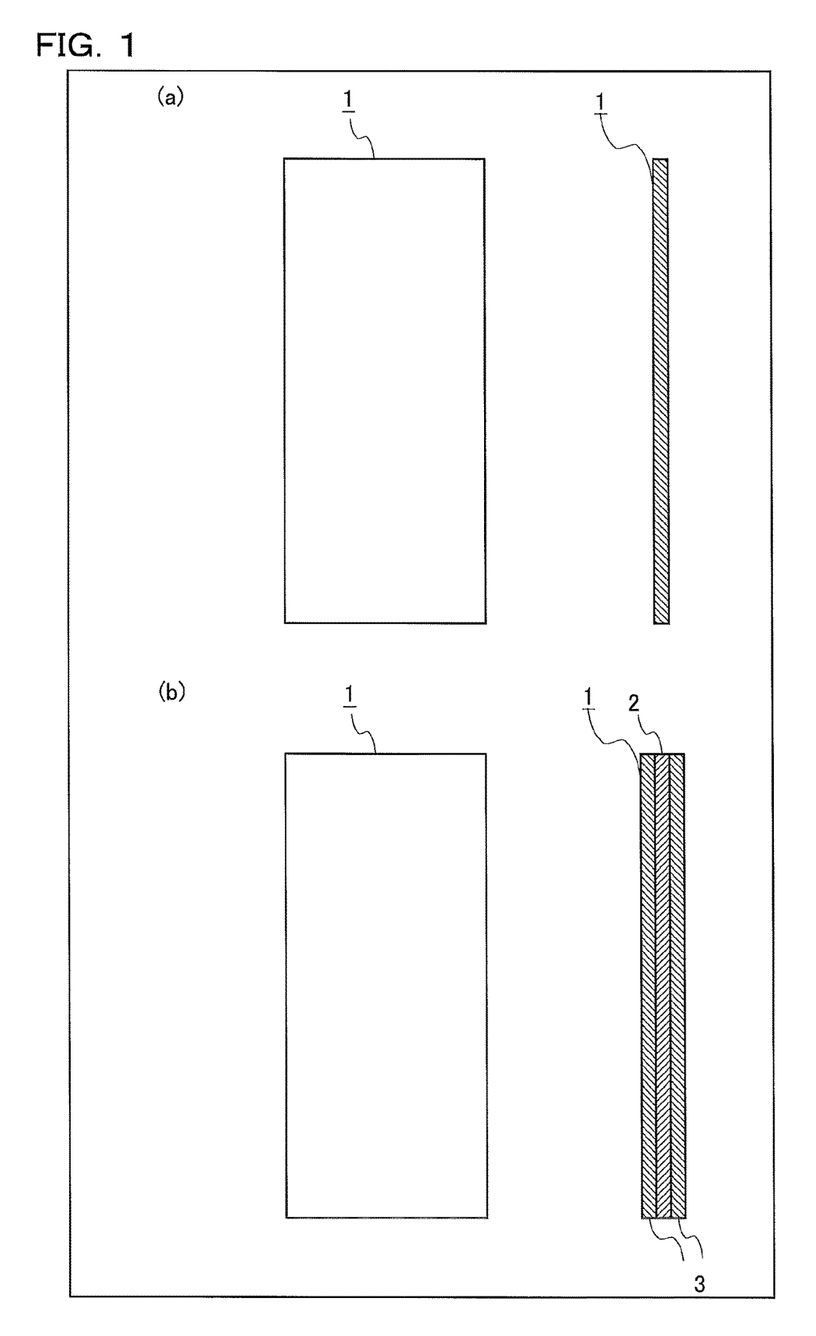
FIG. 1 is a plan view and a cross sectional view an odor adsorbent material according to an embodiment.

In FIG. 1, (a) shows a plan view and a cross sectional view of one example of an odor adsorbent material 1 according to the present embodiment. In this example, the odor adsorbent material 1 is a film consisting of polyethylene alone. The polyethylene film has high absorption capacity against odor components, and odors in open space can be easily transferred thereto. Thus, the polyethylene film can be used as an adsorbent material for odor components.

In FIG. 1, (b) shows a plan view and a cross sectional view of an example of another odor adsorbent material 1 according to the present embodiment. In this example, the odor adsorbent material 1 is a laminated body obtained by laminating polyethylene films 3 on both sides of an elastomer film 2. Alternatively, the elastomer film 2 alone may be used as the odor adsorbent material 1. Furthermore, other materials may be used as the odor adsorbent material 1 as long as it is a material that has high odor adsorption capacity, maintains an adsorptive state for a predetermined time period, and has less odor components in itself such as a resin smell. The odor adsorbent material 1 preferably has an area size not smaller than 100 cm2 for sufficiently adsorbing odor components.

Odor components referred to overall substances having a bad odor or a sweet smell, including mold odor components including haloanisoles such as 2,4,6-trichloroanisole and 2,4,6-tribromoanisole, insect repellents such as naphthalene, agricultural chemicals or fragrances.

2. Odor Detection Kit

Figure 2:
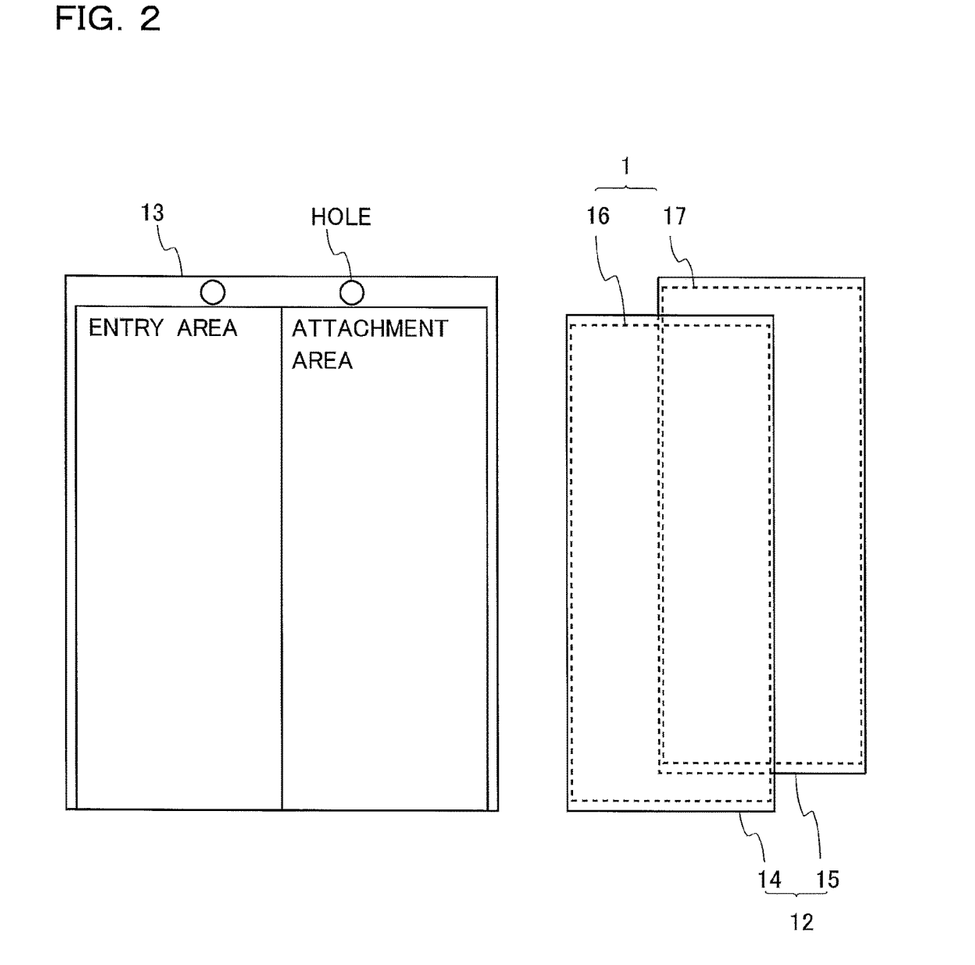
FIG. 2 is a plan view of an odor detection kit according to an embodiment.

FIG. 2 is a plan view of an odor detection kit 11 according to the present embodiment. The odor detection kit 11 includes two pieces of the odor adsorbent material 1, a package section 12, and a sheet section 13. The package section 12 includes two storage sections 14 and 15, and preferably has barrier property. Specifically, an oxygen transmission rate of the package section 12 is, for example, 1 cc/m2/day or lower, and is preferably 0.1 cc/m2/day or lower. The oxygen transmission rate can be measured using, for example, an oxygen transmittance measuring device manufactured by MOCON Inc., in accordance with a measuring method indicated in each specification of ASTM D3985-81 and JIS K 7126B (equal pressure method). Furthermore, a moisture vapor transmission rate is 1 g/m2/day or lower, and is preferably 0.1 g/m2/day or lower. The moisture vapor transmission rate can be measured using, for example, an moisture-vapor transmittance measuring device manufactured by MOCON Inc., in accordance with a measuring method indicated in each specification of ASTM F1249-90 and JIS K 7129B (infrared sensor method). Furthermore, if the package section 12 happens to have an odor, the odor will be adsorbed by the odor adsorbent material 1. Thus, the package section 12 preferably has a low-odor property at a level so as not hamper an organoleptic test using the odor adsorbent material 1.

One example of the package section 12 is a pouch material. The pouch material is formed by, for example, heat-sealing the margin of a laminated body including an aluminium layer. A fastener may be provided at the opening to enable resealing. Various materials can be used as long as the advantageous effect of the present invention is obtained. One of the two pieces of the odor adsorbent material 1 is an exposure adsorbent material 16 that is to be exposed to open space to actually adsorb odors, and the other one of the two pieces is a comparison adsorbent material 17 that is not exposed to open space. The exposure adsorbent material 16 and the comparison adsorbent material 17 are respectively sealed and stored in the storage sections 14 and 15. The exposure adsorbent material 16 and the comparison adsorbent material 17 are preferably manufactured in the same batch and simultaneously stored in the package section 12. With this, the exposure adsorbent material 16 and the comparison adsorbent material 17, at the time point when being stored, are in a state of adsorbing the same substances at the same level, allowing a later described comparison to be performed easily. As long as the comparison can be performed, it is not necessary to have the exposure adsorbent material 16 and the comparison adsorbent material 17 manufactured in the same batch and stored simultaneously. The odor detection kit refers to the odor adsorbent material 1, the package section 12, and the sheet section 13 before being assembled, and also after being assembled.

The storage sections 14 and 15 may be two separate storage bags as shown in FIG. 2, or two storage sections formed in a single package section. Furthermore, the exposure adsorbent material 16 and the comparison adsorbent material 17 may be stored together in either one of the two storage sections 14 and 15.

The sheet section 13 includes an attachment area and an entry area. To the attachment area, the package section 12 and the exposure adsorbent material 16 removed from the package section 12 are attached. For the attachment, the sheet section 13 may have a cut formed thereon, or a pressure sensitive adhesive tape or the like that does not contain an odor component may be used. The sheet section 13 is made from, for example, a paper, and the entry area is used for an entry using a pencil or an ink of a ball-point pen or the like not containing an odor component such as a solvent. With this, it is possible to prevent an entry in the entry area using an ink that contains an odor component, causing the odor component to be adsorbed by the exposure adsorbent material 16. As one example of the sheet section 13, a sheet material having a rectangular shape with a height of 19 cm and a width of 26 cm, and a thickness of 5 mm or smaller may be used.

In the following, one example of the method for using the odor detection kit 11 will be described.

Figure 3:
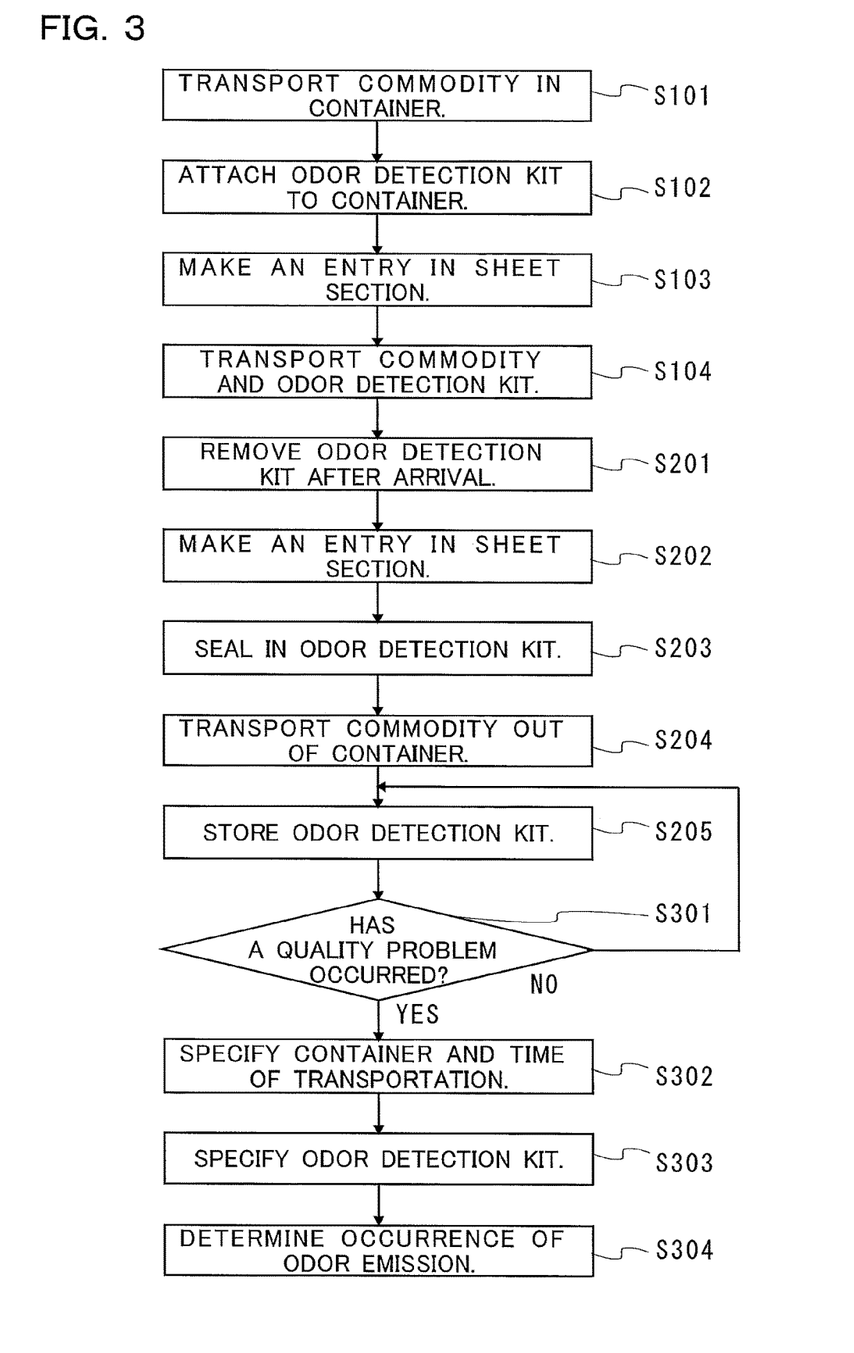
FIG. 3 is a flowchart showing a method for using the odor detection kit according to the embodiment.

The odor detection kit 11 is used at production facilities of a commodity and distribution facilities such as warehouses and containers for transporting and storing a commodity, and is utilized for detecting odor when a quality problem has occurred. FIG. 3 is a flowchart for describing, as one example, one mode of installing, recovering, and testing the odor detection kit 11 used in a container for transportation.

3. Installation Method

In the following, a method for installing the odor detection kit 11 according to one example will be described.

First, a commodity is transported in a container (step S101).

Next, the odor detection kit 11 is attached inside the container (step S102). The odor detection kit 11 is attached by, for example, hooking a hole formed on the sheet section 13 on inner wall of a container door or the like. In addition, the exposure adsorbent material 16 is taken out from the storage section 14, and the package section 12 and the exposure adsorbent material 16 are attached to the sheet section 13. At this moment, the exposure adsorbent material 16 is attached on the uppermost surface to be exposed to open space in the container. The comparison adsorbent material 17 is not taken out from the storage section 15, and is attached to the sheet section 13 while being sealed and stored. When the exposure adsorbent material 16 and the comparison adsorbent material 17 are stored together in either one of the two storage sections 14 and 15, the exposure adsorbent material 16 is taken out, and then the storage section is sealed again while having the comparison adsorbent material 17 stored therein.

Figure 4:
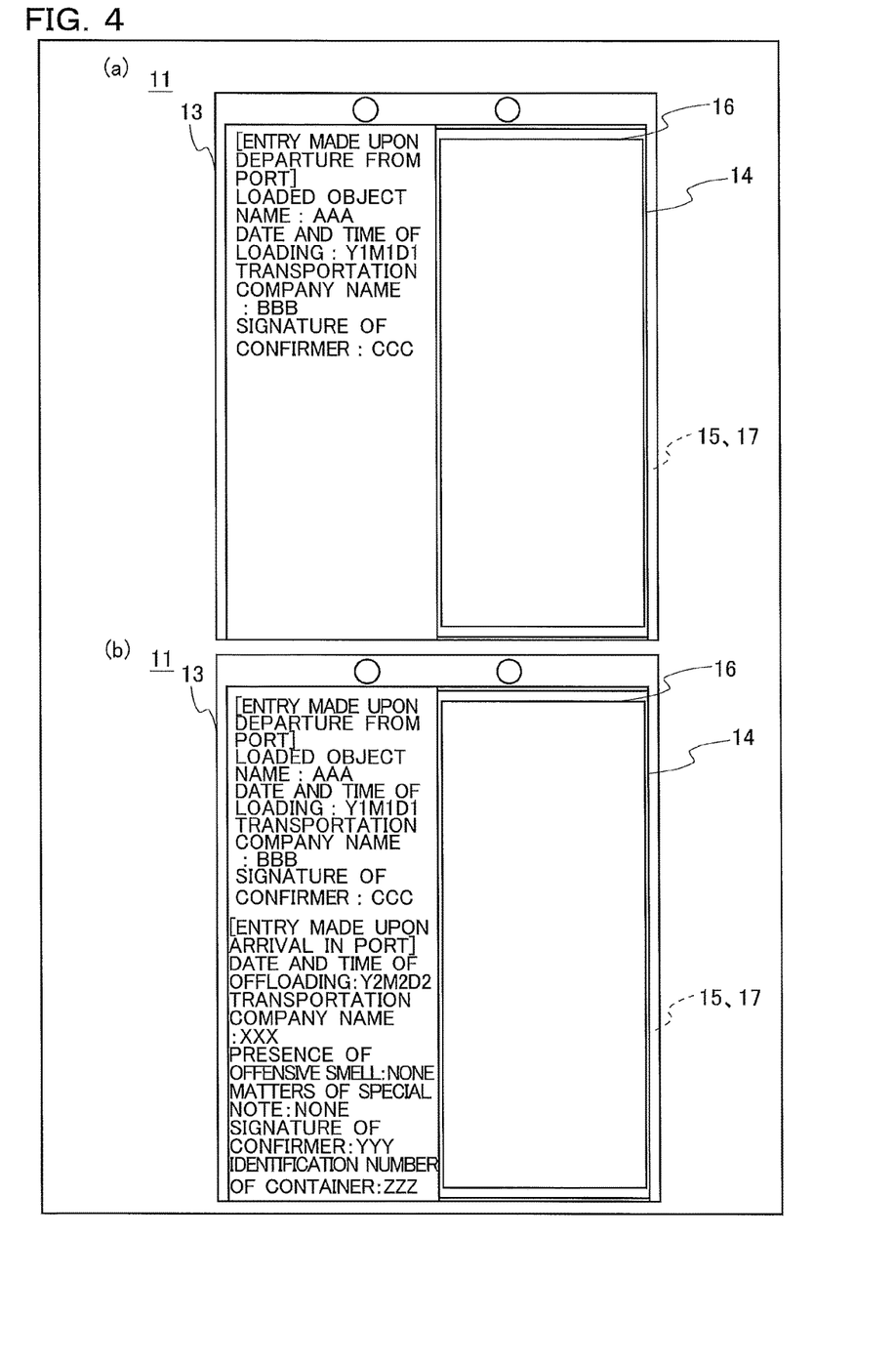
FIG. 4 is a plan view of the odor detection kit according to the embodiment.

Next, information specifying at least the time when the odor detection kit 11 has been installed is entered in the sheet section 13 using a pencil or an ink that does not contain an odor component (step S103). In FIG. 4, (*a*) shows a plan view of the odor detection kit 11 at this stage. In the present embodiment, the name of a loaded object, the date and time of loading, the name of a transportation company, and a signature of a confirmer are entered in the sheet section 13.

The odor detection kit 11 is transported together with the commodity (step S104).

4. Recovery Method

In the following, a method for recovering the odor detection kit 11 according to one example will be described.

When the container arrives at a destination, the odor detection kit 11 is removed (step S201). The exposure adsorbent material 16 is then stored in the package section 12. At this moment, the exposure adsorbent material 16 is stored and sealed in the storage section 14, not the storage section 15 in which the comparison adsorbent material 17 is stored. By sealing in the exposure adsorbent material 16, volatilization of odor components adsorbed by the exposure adsorbent material 16 is prevented. Furthermore, by separating the exposure adsorbent material 16 from the comparison adsorbent material 17, transfer of odor components to the comparison adsorbent material 17 is prevented.

Next, information specifying at least the time when the odor detection kit 11 has been recovered is entered in the sheet section 13 using a pencil or an ink that does not contain an odor component (step S202). In FIG. 4, (*b*) shows a plan view of the odor detection kit 11 at this stage. In the present embodiment, in the sheet section 13, the date and time of shipment, the name of a transportation company, the presence of an offensive smell in a sensory test, matters of special note, a signature of a confirmer, and an identification number of the container are entered. It is preferable to enter, when recovering or installing the odor detection kit 11, information that specifies a facility such as the identification number of the container. With this, the container in which the odor detection kit 11 had been installed can be directly specified later.

Next, the whole odor detection kit 11 is sealed in a pouch material having barrier property and low-odor property (step S203). As the pouch material, for example, a sealing material having an aluminium layer similar to the package section 12 can be used. With this, the possibility of volatilization of an odor component adsorbed by the exposure adsorbent material 16 or the possibility of newly adsorption of an odor component can be reduced with further certainty.

Next, the commodity is transported out of the container (step S204).

Next, the odor detection kit 11 is transported out while being sealed inside the pouch material. The odor detection kit 11 is transported to a predetermined storage location and stored (step S205).

An odor inside the container or the commodity may be performed when the container arrives. When an odor is detected, transporting out the commodity may be stopped. The testing method is not particularly limited, and any predetermined method such as a physicochemical test or an organoleptic test may be executed. In the test, a part of one piece of the exposure adsorbent material 16 may be used.

With the aforementioned installation method and recovery method, when an odor has been emitted in the container, the odor can be adsorbed by the exposure adsorbent material 16, and the exposure adsorbent material 16 that has adsorbed the odor and the sheet section 13 having various information regarding the facility and time of usage etc., can be stored and managed together for a long period of time. It should be noted that the order of steps S101 to S103 may be switched. Furthermore, as long as step S203 is executed after steps S201 and S202, the order of steps S201 to S204 may be switched.

5. Testing Method

In the following, a method for testing the odor detection kit 11 according to one example will be described.

Generally, a commodity is given an identification number such a manufacturing number, and is distributed and provided to a user. A producer or a distributor manages an identification number in association with information that specifies each process in a distribution route. Thus, based on the identification number of the commodity, it is possible to specify a facility used in each of the processes in the distribution route of the commodity, and the time when the facility has been used.

When a quality problem regarding an offensive smell on a commodity has occurred (YES at step S301), first, based on the identification number of the commodity, the container that has transported the commodity and the time of transportation are specified (step S302).

Next, based on information regarding the specified container and time of the transportation, and the content entered in the sheet section 13 of the stored odor detection kit 11, the odor detection kit 11 that has been transported together with the commodity is specified (step S303). The content entered in the sheet section 13 of the odor detection kit 11 is information that specifies the time of transportation and the container to which the odor detection kit 11 has been attached, such as the identification number of the container, the date and time of loading, and the date and time of shipment.

By testing odor components adsorbed by the comparison adsorbent material 17 and the exposure adsorbent material 16 of the specified odor detection kit 11, it is determined whether or not an odor had been emitted in the container (step S304). The method for the odor test is not particularly limited, and the odor test may be executed with any method such as a physicochemical test or an organoleptic test. A test result of the comparison adsorbent material 17 is compared with a test result of the exposure adsorbent material 16 in order to enhance the determination accuracy. Since the comparison adsorbent material 17 had been under the same environment as the exposure adsorbent material 16 except for being sealed also while the container has been transported, if more odor components are detected from the exposure adsorbent material 16 than the comparison adsorbent material 17, the odor components can be determined as being originated from the air within the container with high accuracy. Furthermore, even when odor components are detected from the exposure adsorbent material 16, if the detected odor components are identical to those from the comparison adsorbent material 17 in terms of the type of components and the amounts thereof, the odor components can be determined as not being originated from the air within the container with high accuracy.

With the aforementioned usage method, it is possible to retrospectively determine that an odor had been emitted in a facility in which the odor detection kit 11 had been installed, and rapidly determine whether or not the facility is the cause when a quality problem has occurred. The odor detection kit 11 can be installed, not only in a container for transportation, but also in various facilities involved in each of the processes for the distribution of a commodity, such as each step in a manufacturing plant, a warehouse, and a cargo deck of a truck. When the odor detection kit 11 is installed in each of the facilities, it is possible to rapidly specify a facility in which the odor had been emitted.

6. Modification 1

In the aforementioned embodiment, a mode has been described in which the odor detection kit 11 is installed and recovered when a commodity is transported in and out. However, the odor detection kit 11 may be installed and recovered irrespective of the timing at which a commodity is transported in or out. For example, the odor detection kit 11 may be installed in a factory or a warehouse at any time, and may be recovered after a predetermined time period. Furthermore, the test for odor components may be performed even when a quality problem has not occurred.

It is possible to install, recover, and test the odor detection kit 11 periodically for investigating whether or not an odor had been emitted in a facility such as a factory or a warehouse, and the time when the odor had been emitted.

Figure 5:
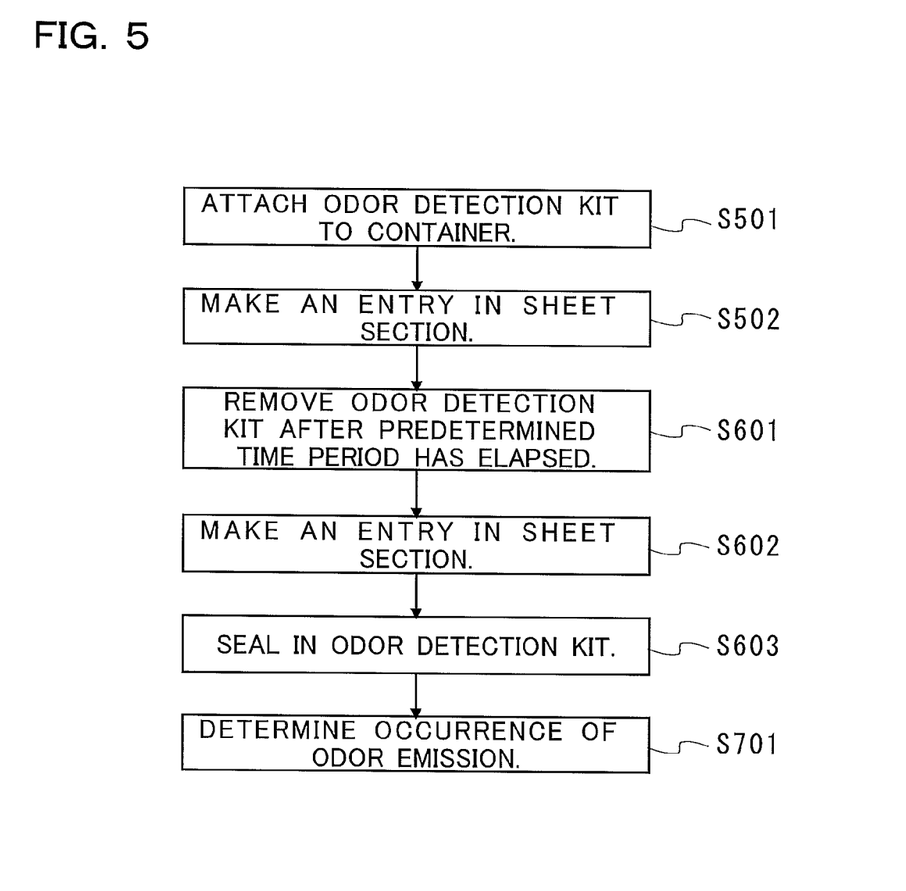
FIG. 5 is a flowchart showing a method for using an odor detection kit according to a modification.

FIG. 5 shows a flowchart for describing one mode of installing, recovering, and testing in the above described case.

First, the odor detection kit 11 is attached inside a facility (step S501). The present step is similar to the aforementioned step S102. The exposure adsorbent material 16 is attached to the uppermost surface of the odor detection kit 11, and is exposed to open space in the facility.

Next, information specifying at least the time when the odor detection kit 11 has been installed is entered in the sheet section 13 using a pencil or an ink that does not contain an odor component (step S502). The present step is similar to the aforementioned step S103. In the present modification, in the sheet section 13, for example, the name of facility, the date and time of installation, and a signature of a confirmer are entered.

After the predetermined time period has elapsed since installing the odor detection kit 11, the odor detection kit 11 is removed (step S601). The present step is similar to the aforementioned step S201. The exposure adsorbent material 16 is sealed and stored in the package section 12 separately from the comparison adsorbent material 17.

Next, information specifying at least the time when the odor detection kit 11 has been recovered is entered in the sheet section 13 using a pencil or an ink that does not contain an odor component (step S602). The present step is similar to the aforementioned step S202. In the present modification, in the sheet section 13, for example, the date and time of recovery and a signature of a confirmer are entered. It is also possible to perform the test of odor inside the facility when recovering the odor detection kit 11, and enter the result in the sheet section 13.

Next, the whole odor detection kit 11 is sealed in a pouch material having barrier property and odorless property (step S603). The present step is similar to the aforementioned step S203.

Next, the odor detection kit 11 is transported to a test site while being sealed in the pouch material, and the test is performed thereon (step S701). By testing odor components adsorbed by the comparison adsorbent material 17 and the exposure adsorbent material 16 of the odor detection kit 11, it is determined whether or not an odor had been emitted in the facility within the predetermined time period. The determination method is similar to the method in the aforementioned step S304.

In the present modification, emission of an odor in a facility within the predetermined time period can be investigated without constantly placing a person in the facility. The predetermined time period is a period of time determined discretionarily, and may be, for example, one week or one month. The time of odor emission can be specified more precisely when the predetermined time period from installation to recovery of the odor detection kit 11 is shortened. If the present modification is applied in, for example, a warehouse prior to storing a commodity, it becomes possible to determine whether a quality problem may occur in the warehouse beforehand, and reduce the occurrence of a quality problem.

7. Modification 2

In the aforementioned embodiment, although an example in which the odor detection kit 11 includes two pieces of the odor adsorbent material 1 has been described, the odor detection kit 11 may include, as a modification, a plurality of pieces of three pieces or more of the odor adsorbent material 1. In this case, the plurality of pieces of the odor adsorbent material 1 are used as the exposure adsorbent material 16, and the plurality of pieces of the exposure adsorbent material 16 may be installed at multiple locations in the facility to enable improvement in precision of odor detection. Furthermore, a plurality of pieces of the odor adsorbent material 1 may be used as the comparison adsorbent material 17.

8. Modification 3

In the aforementioned embodiment, although the method for using the odor detection kit 11 has been described, the odor adsorbent material 1 may be used by itself as a modification. That is, the odor adsorbent material 1 is taken out from the package section and then attached directly inside the facility as the exposure adsorbent material 16 without being attached to the sheet section 13. Furthermore, the package section is not limited to the pouch material, as long as the package section has a certain level of barrier property and low-odor property and can prevent odors from being adsorbed by the odor adsorbent material 1. For example, instead of the pouch material, the odor adsorbent material 1 may be packaged in an aluminium foil. Furthermore, instead of installing the comparison adsorbent material 17 in the facility, the odor adsorbent material 1 that has not been exposed may be stored in a predetermined location to be used as the comparison adsorbent material 17. Still further, it is possible to not use the comparison adsorbent material 17. For example, emission of an odor inside the facility can be determined by only comparing odor test results from an organoleptic test of the exposure adsorbent material 16 when being attached inside the facility and after being recovered therefrom.

As described above, embodiments according to the present invention are useful for odor tests etc., in facilities for producing and distributing commodities such as food products.

DESCRIPTION OF THE REFERENCE CHARACTERS 1 odor adsorbent material
2 elastomer film
3 polyethylene film
11 odor detection kit
12 package section
13 sheet section
14, 15 storage section
16 exposure adsorbent material
17 comparison adsorbent material

The invention claimed is:
1. A method for recovering an odor detection kit, the method including:
removing an odor detection kit installed in a facility for production or distribution of a commodity, the odor detection kit including
a first odor adsorbent material and a second odor adsorbent material;
a package section that includes a first storage section capable of storing the first odor adsorbent material and a second storage section capable of storing the second odor adsorbent material; and
a sheet section, wherein
the first odor adsorbent material is sealed in the first storage section,
the second odor adsorbent material is exposed to an external open space located in the facility, the open space being an odor detection target, and
the first storage section and the second odor adsorbent material are installed in the open space;
storing and sealing, in the second storage section, the second odor adsorbent material exposed to the open space in the facility;
entering, in the sheet section, information that specifies at least a time when the odor detection kit has been recovered; and
after the sealing and the entering, sealing the odor detection kit in a pouch material that has barrier property and odorless property.
2. The method for recovering the odor detection kit according to claim 1, wherein the method is conducted when transporting a commodity out of the facility.
3. The method for recovering the odor detection kit according to claim 1, the method further including entering, in the sheet section, information that specifies the facility.
4. A method for testing the odor detection kit recovered by the method for recovering the odor detection kit according to claim 3, the method including:
specifying, based on an identification number given to a commodity, a facility used in production and distribution processes of the commodity and a time of usage; and
selecting the odor detection kit that is to be a subject for testing, based on the specified facility and time of usage, and information that specifies a time of usage and a facility entered in the sheet section of the odor detection kit.
5. An odor testing method including:
installing, in an exposed state, at least one piece of an odor adsorbent material having been packaged in a condition that prevented adsorption of odor outside of a packaging of the odor adsorbent material, in a facility for production or distribution of a commodity, such that a first piece of the odor adsorbent material is installed in the facility in an exposed state of being exposed to open space in the facility;
recovering the first piece of the odor adsorbent material installed in the facility;
testing at least odor components adsorbed by the recovered first piece of the odor adsorbent material;
comparing a test result obtained from the testing with a comparison result, which is a result of testing odor components adsorbed by a second piece of the odor adsorbent material in a blank state, the blank state being a state other than the exposed state of being exposed to the open space, to thereby determine a difference between the test result and the comparison result; and
determining whether an odor has been emitted in the facility based on the determined difference between the test result and the comparison result.
6. The odor testing method according to claim 5, further including:
testing an odor component adsorbed by the second piece of the odor adsorbent material at a time point when the odor adsorbent material had been installed, wherein
the comparison result includes a result of the testing of an odor component adsorbed by the second piece of the odor adsorbent material at the time point when the odor adsorbent material had been installed.
7. The odor testing method according to claim 5, wherein at least an organoleptic test is performed at one of or both of:
the testing of an odor component adsorbed by the recovered first piece of the odor adsorbent material; and the testing of an odor component adsorbed by the odor adsorbent material at a time point when the odor adsorbent material had been installed.

8. The odor testing method according to claim 5, wherein the installing of the odor adsorbent material in the exposed state is conducted when transporting the commodity in the facility.

9. The odor testing method according to claim 5, wherein the recovering of the odor adsorbent material is conducted when transporting the commodity out of the facility.

10. The odor testing method according to claim 5, wherein the odor adsorbent material has a sheet shape.

11. The odor testing method according to claim 10, wherein the odor adsorbent material is formed by laminating polyethylene on both sides of an elastomer film.

12. The odor testing method according to claim 10, wherein the odor adsorbent material has an area size not smaller than 100 $cm^2$.

13. The odor testing method according to claim 10, wherein, at the installing of the odor adsorbent material in the exposed state, the installing is conducted by having at least one surface of the odor adsorbent material uncovered.

14. The odor testing method according to claim 5, wherein the odor adsorbent material adsorbs substances having a bad odor or a sweet smell, including mold odor components including haloanisoles, insect repellents such as naphthalene, agricultural chemicals or fragrances.

15. The odor testing method according to claim 5, wherein the blank state is a state of remaining sealed and stored inside the packaging.

\* \* \* \* \*